United States Patent [19]
Coleman et al.

[11] Patent Number: 5,945,506
[45] Date of Patent: Aug. 31, 1999

[54] CHEMOKINE EXPRESSED IN FETAL SPLEEN AND ITS PRODUCTION

[75] Inventors: Roger Coleman, Mountain View; Craig G. Wilde, Sunnyvale; Jeffrey J. Seilhamer, Los Altos Hills, all of Calif.

[73] Assignee: Incyte Pharmaceuticals, Inc., Palo Alto, Calif.

[21] Appl. No.: 08/467,123

[22] Filed: Jun. 6, 1995

Related U.S. Application Data

[62] Division of application No. 08/375,346, Jan. 19, 1995, Pat. No. 5,605,817.

[51] Int. Cl.$^6$ ............... C07K 14/52; C12N 15/19; C12N 15/63; C12N 5/10
[52] U.S. Cl. ............... 530/324; 435/69.5; 435/325; 435/471; 435/252.3; 435/320.1; 435/71.1; 435/71.2; 930/140; 536/23.5
[58] Field of Search ............... 530/300, 324; 930/140; 435/69.5, 240.2, 252.3, 320.1, 71.1, 71.2, 471, 325; 536/23.5

[56] References Cited

PUBLICATIONS

*Banchereau, J., "Interleukin–4," *The Cytokine Handbook*, Academic Press, Chapter 6, pp. 120–148 (1991).
*Schall, T. J., "The Chemokines," *The Cytokine Handbook*, Academic Press, Second Edition, pp. 180–272 (1994).
*Shaw, A. R., "Molecular Biology of Cytokines," *The Cytokine Handbook*, Academic Press, Chapter 2, pp. 20–46 (1991).
*Vilcek et al., "Immunology of Cytokines," *The Cytokine Handbook*, Academic Press, Chapter 1, pp. 1–17 (1991).
Nakao et al. (1990) Mol. & Cell. Biol. vol. 10, No. 7, pp. 3646–3658.
Goodman et al. (1992) Biochemistry vol. 31 pp. 10483–10490.

*Primary Examiner*—Prema Mertz
*Attorney, Agent, or Firm*—Incyte Pharmaceuticals, Inc.

[57] ABSTRACT

The present invention provides nucleotide and amino acid sequences that identify and encode a novel expressed chemokine (FSEC) from human fetal spleen cells. The present invention also provides for antisense molecules to the nucleotide sequences which encode FSEC, expression vectors for the production of purified FSEC, antibodies capable of binding specifically to FSEC, hybridization probes or oligonucleotides for the detection of FSEC-encoding nucleotide sequences, genetically engineered host cells for the expression of FSEC, diagnostic tests for chemokine activation based on FSEC-encoding nucleic acid molecules and antibodies capable of binding specifically to the protein.

2 Claims, 4 Drawing Sheets

```
            157         166         175         184         193         202
5' ATG GCC CTG CTA CTG GCC CTC AGC CTG CTG GTT CTC TGG ACT TCC CCA GCC CCA
   M   A   L   L   L   A   L   S   L   L   V   L   W   T   S   P   A   P 211         220         229         238         247         256
   ACT CTG AGT GGC ACC AAT GAT GCT GAA GAC TGC TGC CTG TCT GTG ACC CAG AAA
   T   L   S   G   T   N   D   A   E   D   C   C   L   S   V   T   Q   K 265         274         283         292         301         310
   CCC ATC CCT GGG TAC ATC GTG AGG AAC TTC CAC TAC CTT CTC ATC AAG GAT GGC
   p   I   P   G   Y   I   V   R   N   F   H   Y   L   L   I   K   D   G 319         328         337         346         355         364
   TGC AGG GTG CCT GCT GTA GTG TTC ACC ACA CTG AGG GGC CGC CAG CTC TGT GCA
   C   R   V   P   A   V   V   F   T   T   L   R   G   R   Q   L   C   A 373         382         391         400         409         418
   CCC CCA GAC CAG CCC TGG GTA GAA CGC ATC ATC CAG AGA CTG CAG AGG ACC TCA
   p   p   D   Q   P   W   V   E   R   I   I   Q   R   L   Q   R   T   S 427         436         445
   GCC AAG ATG AAG CGC CGC AGC AGT TAA  3'
   A   K   M   K   R   R   S   S   *
```

FIG. 1

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 719 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (A) LIBRARY: HUMAN FETAL SPLEEN
       (B) CLONE: 29592

(xi) SEQUENCE DESCRIPTION: SEQ ID NO:1:

GCAGGGCTCA CATTCCCAGC CTCACATCAC TCACACCTTG CATTTCACCC CTGCATCCCA    60

GTCGCCCTGC AGCCTCACAC AGATCCTGCA CACACCCAGA CAGCTGGCGC TCACACATTC   120

ACCGTTGGCC TGCCTCTGTT CACCCTCCAT GGCCCTGCTA CTGGCCCTCA GCCTGCTGGT   180

TCTCTGGACT TCCCCAGCCC CAACTCTGAG TGGCACCAAT GATGCTGAAG ACTGCTGCCT   240

GTCTGTGACC CAGAAACCCA TCCCTGGGTA CATCGTGAGG AACTTCCACT ACCTTCTCAT   300

CAAGGATGGC TGCAGGGTGC CTGCTGTAGT GTTCACCACA CTGAGGGGCC GCCAGCTCTG   360

TGCACCCCCA GACCAGCCCT GGGTAGAACG CATCATCCAG AGACTGCAGA GGACCTCAGC   420

CAAGATGAAG CGCCGCAGCA GTTAACCTAT GACCGTGCAG AGGGAGCCCG GAGTCCGAGT   480

CAAGCATTGT GAATTATTAC CTAACCTGGG GAACCGAGGA CCAGAAGGAA GGACCAGGCT   540

TCCAGCTCCT CTGCACCAGA CCTGACCAGC CAGGACAGGG CCTGGGGTGT GTGTGAGTGT   600

GAGTGTGAGC GAGAGGGTGA GTGTGGTCAG AGTAAAGCTG CTCCACCCCC AGATTGCAAT   660

GCTACCAATA AAGCCGCCTG GTGTTTACAA CTAAAAAAAA AAAAAAAAAA AAAAAAAA    719

(2) INFORMATION FOR SEQ ID NO:2:

(i) SEQUENCE CHARACTERISTICS:
       (A) LENGTH: 98 amino acids
       (B) TYPE: amino acid
       (C) STRANDEDNESS: single
       (D) TOPOLOGY: linear (ii) MOLECULE TYPE: peptide (vii) IMMEDIATE SOURCE:
       (A) LIBRARY: HUMAN FETAL SPLEEN
       (B) CLONE: 29592

(xi) SEQUENCE DESCRIPTION: SEQ ID NO:2:

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser (2) INFORMATION FOR SEQ ID NO:3:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
                35                  40                  45

Asp Tyr Phe Glu Thr Ser Ser Gln Cys Ser Lys Pro Gly Val Ile Phe
50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

(2) INFORMATION FOR SEQ ID NO:4:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
                35                  40                  45

Val Asp Tyr Tyr Glu Thr Ser Ser Leu Cys Ser Gln Pro Ala Val Val
50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

(2) INFORMATION FOR SEQ ID NO:5:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Lys Val Ser Ala Ala Arg Leu Ala Val Ile Leu Ile Ala Thr Ala
 1               5                  10                  15
Leu Cys Ala Pro Ala Ser Ala Ser Pro Tyr Ser Ser Asp Thr Thr Pro
                20                  25                  30
Cys Cys Phe Ala Tyr Ile Ala Arg Pro Leu Pro Arg Ala His Ile Lys
                35                  40                  45
Glu Tyr Phe Tyr Thr Ser Gly Lys Cys Ser Asn Pro Ala Val Val Phe
                50                  55                  60
Val Thr Arg Lys Asn Arg Gln Val Cys Ala Asn Pro Glu Lys Lys Trp
 65                  70                  75                  80
Val Arg Glu Tyr Ile Asn Ser Leu Glu Met Ser
                85                  90
```

(2) INFORMATION FOR SEQ ID NO:6:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Gly Leu Ala Ala Ala Leu Leu Val Leu Val Cys Thr Met Ala Leu Cys
 1               5                  10                  15
Ser Cys Ala Gln Val Gly Thr Asn Lys Glu Leu Cys Cys Leu Val Tyr
                20                  25                  30
Thr Ser Trp Gln Ile Pro Gln Lys Phe Ile Val Asp Tyr Ser Glu Thr
                35                  40                  45
Ser Pro Gln Cys Pro Lys Pro Gly Val Ile Leu Leu Thr Lys Arg Gly
                50                  55                  60
Arg Gln Ile Cys Ala Asp Pro Asn Lys Lys Trp Val Gln Lys
 65                  70                  75
```

2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TCCTTCCTTC TGGTCCTCGG TTCC                                      24

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GGAAACAGCT ATGACCATG                                        19

(2) INFORMATION FOR SEQ ID NO:9:

(i) SEQUENCE CHARACTERISTICS:

```
          (A) LENGTH: 31 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:9:

CTTGGAATTC ACTCCGGGCT CCCTCTGCAC G                                    31
```

CHEMOKINE EXPRESSED IN FETAL SPLEEN AND ITS PRODUCTION

This application is a division of application Ser. No. 08/375,346, filed Jan. 19, 1995, now U.S. Pat. No. 5,605,817.

BACKGROUND OF THE INVENTION

In humans, the spleen serves at least four major physiologic functions. First, as part of the peripheral immune system, it clears the blood of microorganisms and particulate antigens and/or generates antigens to foreign substances. Second, it sequesters and removes excess, old and/or abnormal blood cells. Third, its vasculature is involved in the regulation of portal blood flow. Finally, it engages in hematopoiesis during development or when the bone marrow alone cannot produce sufficient blood cells.

The spleen consists of red pulp which contains blood-filled sinuses and pulp cords lined by reticuloendothelial cells and of white pulp which is arranged around a central arteriole. The surrounding periarteriolar lymphoid sheath (PALS) contains both T and B cell areas. The T cell area lies adjacent to the arteriole and consists of small, densely packed lymphocytes, primarily $T4^+$ helper T lymphocytes. Outside of the T cell area is the follicular zone which contains B lymphocytes and germinal centers which are made up of B cells and macrophages. The white pulp is surrounded by a marginal zone containing specialized, antigen-presenting macrophages and B cells.

Blood-borne lymphocytes enter the red and white pulp via the trabecular artery. Most branches empty into or near the marginal zones; but some end in the white pulp and supply oxygen and nutrients to the germinal centers and outer mantle zones, and others run directly into the red pulp. T and B lymphocytes pass through the spleen at different rates. B cells generally migrate through the tissue more slowly, but they eventually cross into the red pulp and exit the spleen via the splenic vein.

In the spleen as well as other tissues, leukocytes including monocytes, macrophages, basophils, and eosinophils play important roles in the pathological mechanisms initiated by T and/or B lymphocytes. Macrophages, in particular, produce powerful oxidants and proteases which contribute to tissue destruction and secrete a range of cytokines which recruit and activate other inflammatory cells.

The investigation of the critical, regulatory processes by which white cells proceed to their appropriate destination and interact with other cells is underway. The current model of leukocyte movement or trafficking from the blood to injured or inflamed tissues comprises the following steps. The first step is the rolling adhesion of the leukocyte along the endothelial cells of the blood vessel wall. This movement is mediated by transient interactions between selectins and their ligands. A second step involves cell activation which promotes a more stable leukocyte-endothelial cell interaction mediated by the integrins and their ligands. This stronger, more stable adhesion precipitates the final steps—leukocyte diapedesis and extravasation into the tissues.

The chemokine family of polypeptide cytokines possesses the cellular specificity required to explain leukocyte trafficking in different abnormal, inflammatory or diseased situations. First, chemokines mediate the expression of particular adhesion molecules on endothelial cells; and second, they generate gradients of chemoattractant factors which activate specific cell types. In addition, the chemokines stimulate the proliferation of specific cell types and regulate the activation of cells which bear specific receptors. These activities demonstrate a high degree of target cell specificity.

The chemokines are small polypeptides, generally about 70–100 amino acids (aa) in length, 8–11 kD in molecular weight and active over a 1–100 ng/ml concentration range. Initially, they were isolated and purified from inflamed tissues and characterized relative to their bioactivity. More recently, chemokines have been discovered through molecular cloning techniques and characterized by structural as well as functional analysis.

The chemokines are related through a four-cysteine motif which is based primarily on the spacing of the first two cysteine residues in the mature molecule. Currently the chemokines are assigned to one of two families, the C-C chemokines ($\alpha$) and the C-X-C chemokines ($\beta$). Although exceptions exist, the C-X-C chemokines generally activate neutrophils and fibroblasts while the C-C chemokines act on a more diverse group of target cells which include monocytes/macrophages, basophils, eosinophils, T lymphocytes and others. The known chemokines of both families are synthesized by many diverse cell types as reviewed in Thomson A. (1994) The Cytokine Handbook, 2d Ed. Academic Press, NY. The two groups of chemokines will be described in turn.

At this time, relatively few C-C chemokines have been described, and they appear to have less N-terminal processing than the C-X-C chemokines. A brief description of the known human (and/or murine) C-C chemokines follows. The macrophage inflammatory proteins alpha and beta (MIP-1 $\alpha$ and $\beta$) were first purified from stimulated mouse macrophage cell line and elicited an inflammatory response when injected into normal tissues. At least three distinct and non-allelic genes encode human MIP-1 $\alpha$, and seven distinct genes encode MIP-1 $\beta$.

MIP-1 $\alpha$ and MIP-1 $\beta$ consist of 68–69 aa which are about 70% identical in their acidic, mature secreted forms. They are both expressed in stimulated T cells, B cells and monocytes in response to mitogens, anti-CD3 and endotoxin, and both polypeptides bind heparin. While both molecules stimulate monocytes, MIP-1 $\alpha$ chemoattracts the CD-8 subset of T lymphocytes and eosinophils, while MIP-1 $\beta$ chemoattracts the CD-4 subset of T lymphocytes. In mouse, these proteins are known to stimulate myelopoiesis.

I-309 was cloned from a human $\gamma$-$\delta$ T cell line and shows 42% aa identity to T cell activation gene 3 (TCA3) cloned from mouse. There is considerable nucleotide homology between the 5' flanking regions of these two proteins, and they share an extra pair of cysteine residues not found in other chemokines. Such similarities suggest I-309 and TCA3 are species homologs which have diverged over time in both sequence and function.

RANTES is another C-C chemokine which is expressed in T cells (but not B cells), in platelets, in some tumor cell lines, and in stimulated rheumatoid synovial fibroblasts. In the latter, it is regulated by interleukins-1 and -4, transforming nerve factor and interferon-$\gamma$. The cDNA cloned from T cells encodes a basic 8 kD protein which lacks N-linked glycosylation and is able to affect lymphocytes, monocytes, basophils and eosinophils. The expression of RANTES mRNA is substantially reduced following T cell stimulation.

Monocyte chemotactic protein (MCP-1) is a 76 aa protein which appears to be expressed in almost all cells and tissues upon stimulation by a variety of agents. The targets of MCP-1, however, are limited to monocytes and basophils in which it induces a MCP-1 receptor:G protein-linked calcium flux (Charo I, personal communication). Two other related proteins (MCP-2 and MCP-3) were purified from a human osteosarcoma cell line. MCP-2 and MCP-3 have 62% and 73% aa identity, respectively, with MCP-1 and share its chemoattractant specificity for monocytes.

Current techniques for diagnosis of abnormalities in the inflamed or diseased tissues mainly rely on observation of clinical symptoms or serological analyses of body tissues or fluids for hormones, polypeptides or various metabolites. Patients often manifest no clinical symptoms at early stages of disease or tumor development. Furthermore, serological analyses do not always differentiate between invasive diseases and genetic syndromes which have overlapping or very similar ranges. Thus, development of new diagnostic techniques comprising small molecules such as the expressed chemokines are important to provide for early and accurate diagnoses, to give a better understanding of molecular pathogenesis, and to use in the development of effective therapies.

The chemokine molecules were reviewed in Schall T J (1994) Chemotactic Cytokines: Targets for Therapeutic Development. International Business Communications, Southborough, Mass., pp 180–270; and in Paul W E (1993) Fundamental Immunology, Raven Press, New York City (NYC), pp 822–826.

SUMMARY OF THE INVENTION

The subject invention provides a nucleotide sequence which uniquely encodes a novel human fetal spleen protein. The new gene, which is known as fetal spleen expressed chemokine, or fsec (Incyte Clone 29592), encodes a polypeptide designated FSEC, of the C-C chemokine family. The invention also comprises diagnostic tests for physiologic or pathologic compromise of the spleen which include the steps of testing a sample or an extract thereof with fsec DNA, fragments or oligomers thereof. Aspects of the invention include the antisense DNAs of fsec; cloning or expression vectors containing fsec; host cells or organisms transformed with expression vectors containing fsec; a method for the production and recovery of purified FSEC from host cells; and purified FSEC.

DESCRIPTION OF THE FIGURES

FIG. 1 displays the nucleotide sequence for fsec and the predicted amino acid (aa) sequence of the fetal spleen expressed chemokine, FSEC.

DETAILED DESCRIPTION OF THE INVENTION

Definitions

Figure 2:
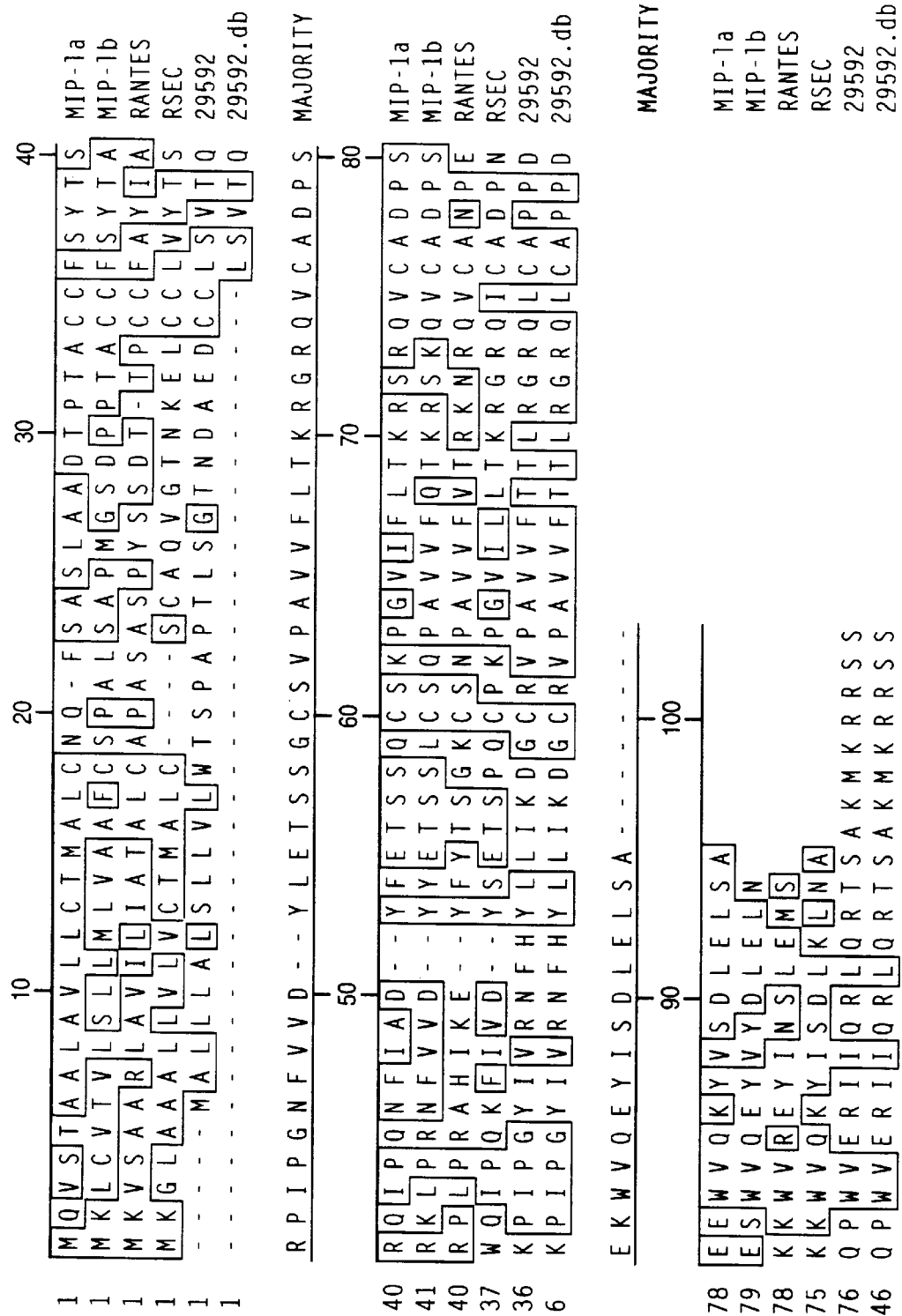
FIG. 2 shows the aa alignment of FSEC with other human chemokines of the C-C family. Alignments shown were produced using the multisequence alignment program of DNASTAR software (DNASTAR Inc, Madison Wis.).

As used herein, "fetal spleen expressed chemokine" or FSEC, refers to a polypeptide, a naturally occurring FSEC or active fragments thereof, which is encoded by an mRNA transcribed from fsec cDNA of Seq ID No 1.

"Active" refers to those forms of FSEC which retain the biologic and/or immunologic activities of naturally occurring FSEC.

"Naturally occurring FSEC" refers to FSEC produced by human cells that have not been genetically engineered and specifically contemplates various FSEC forms arising from post-translational modifications of the polypeptide including but not limited to acetylation, carboxylation, glycosylation, phosphorylation, lipidation and acylation.

"Derivative" refers to polypeptides derived from naturally occurring FSEC by chemical modifications such as ubiquitination, labeling (e.g., with radionuclides, various enzymes, etc.), pegylation (derivatization with polyethylene glycol) or by insertion or substitution by chemical synthesis of aa such as ornithine, which do not normally occur in human proteins.

"Recombinant variant" refers to any polypeptide differing from naturally occurring FSEC by aa insertions, deletions, and substitutions, created using recombinant DNA techniques. Guidance in determining which aa residues may be replaced, added or deleted without abolishing activities of interest, such as cell adhesion and chemotaxis, may be found by comparing the sequence of the particular FSEC with that of homologous cytokines and minimizing the number of aa sequence changes made in regions of high homology.

Preferably, aa "substitutions" are the result of replacing one aa with another aa having similar structural and/or chemical properties, such as the replacement of a leucine with an isoleucine or valine, an aspartate with a glutamate, or a threonine with a serine, i.e., conservative aa replacements. "Insertions" or "deletions" are typically in the range of about 1 to 5 aa. The variation allowed may be experimentally determined by systematically making insertions, deletions, or substitutions of aa in FSEC using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of aa residues of at least about 5 amino acids, often at least about 7 aa, typically at least about 3 to 13 aa, and, in various embodiments, at least about 17 or more aa. To be active, FSEC polypeptide must have sufficient length to display biologic and/or immunologic activity.

An "oligonucleotide" or polynucleotide "fragment", "portion," or "segment" is a stretch of nucleotide residues which is long enough to use in polymerase chain reaction (PCR) or various hybridization procedures to amplify or simply reveal related parts of mRNA or DNA molecules.

The present invention includes purified FSEC polypeptides from natural or recombinant sources, cells transformed with recombinant nucleic acid molecules encoding FSEC. Various methods for the isolation of the FSEC polypeptides may be accomplished by procedures well known in the art. For example, such polypeptides may be purified by immunoaffinity chromatography by employing the antibodies provided by the present invention. Various other methods of protein purification well known in the art include those described in Deutscher M (1990) Methods in Enzymology, Vol 182, Academic Press, San Diego; and Scopes R (1982) Protein Purification: Principles and Practice. Springer-Verlag, NYC, both incorporated herein by reference.

"Recombinant" may also refer to a polynucleotide which encodes FSEC and is prepared using recombinant DNA techniques. The DNA which encodes FSEC may also include allelic or recombinant variants and mutants thereof.

"Oligonucleotides" or "nucleic acid probes" are prepared based on the cDNA sequence which encodes FSEC provided by the present invention. Oligonucleotides comprise portions of the DNA sequence having at least about 15 nucleotides, usually at least about 20. nucleotides. Nucleic acid probes comprise portions of the sequence having fewer nucleotides than about 6 kb, usually fewer than about 1 kb. After appropriate testing to eliminate false positives, these probes may be used to determine whether mRNA encoding FSEC is present in a cell or tissue or to isolate similar nucleic acid sequences from chromosomal DNA as described by Walsh PS et al (1992 PCR Methods Appl 1:241–250).

Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, NY; or Ausubel FM et al (1989) Current Protocols in Molecular Biology, John Wiley & Sons, NYC, both incorporated herein by reference.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryptic or eukaryotic system. Mutations may also be introduced to modify the properties of the polypeptide, to change ligand-binding affinities, interchain affinities, or polypeptide degradation or turnover rate.

Detailed Description of the Invention

The present invention provides a nucleotide sequence uniquely identifying a novel chemokine of the C-C family, FSEC, which is highly expressed in the fetal spleen. Because FSEC is specifically expressed in fetal spleen, the nucleic acid (fsec), polypeptide (FSEC) and antibodies to FSEC are useful in diagnostic assays based on chemokine production in cases of inflammation or disease affecting the fetal spleen. Excessive expression of FSEC leads to activation of monocytes, macrophages, basophils, eosinophils, T lymphocytes and/or other cells which respond by producing abundant proteases and other molecules which can lead to tissue damage or destruction. Therefore, a diagnostic test for excess expression of FSEC can accelerate diagnosis and proper treatment of an abnormal condition caused by viral or bacterial infections including mononucleosis, malaria or AIDS; mechanical injury associated with trauma; diseases affecting immunoregulation such as rheumatoid arthritis or systemic lupus erythematosis; diseases of erythrocytes or blood flow including sickle cell anemia and β thalassemia; infiltrative diseases such as leukemias and lymphomas; or other physiologic and pathologic problems which affect the function of the organ.

The nucleotide sequences encoding FSEC (or their complement) have numerous applications in techniques known to those skilled in the art of molecular biology. These techniques include use as hybridization probes, use as oligomers for PCR, use for chromosome and gene mapping, use in the recombinant production of FSEC, and use in the generation of anti-sense DNA or RNA, their chemical analogs and the like. Uses of nucleotides encoding FSEC disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of FSEC-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring FSEC, and all such variations are to be considered as being specifically disclosed.

Although nucleotide sequences which encode FSEC and/or FSEC variants are preferably capable of hybridizing to the nucleotide sequence of the naturally, occurring FSEC gene under stringent conditions, it may be advantageous to produce nucleotides sequences encoding FSEC or FSEC derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding FSEC and/or FSEC derivatives without altering the encoded aa sequence include the production of RNA transcripts having more desirable properties, such as a greater half-life, than transcripts produced from the naturally occurring sequence.

Nucleotide sequences encoding FSEC may be joined to a variety of other nucleotide sequences by means of well established recombinant DNA techniques (cf Sambrook J et al. (1989) Molecular Cloning: A Laboratory Manual, Cold Spring Harbor Laboratory, NY). Useful nucleotide sequences for joining to fsec include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for fsec-specific nucleic acid hybridization probes capable of hybridizing with naturally occurring nucleotide sequences encoding FSEC. Such probes may also be used for the detection of similar chemokine encoding sequences and should preferably contain at least 50% of the nucleotides from a C-C encoding sequence. The hybridization probes of the subject invention may be derived from the nucleotide sequences of the SEQ ID NO 1 or from genomic sequences including promoters, enhancer elements and introns of naturally occurring fsec. Hybridization probes may be labeled by a variety of reporter groups, including radionuclides such as 32P or 35S, or enzymatic labels such as alkaline phosphatase coupled to the probe via avidin/biotin coupling systems, and the like.

PCR as described U.S. Pat. Nos. 4,683,195; 4,800,195; and 4,965,188 provides additional uses for oligonucleotides based upon the nucleotide sequences which encode FSEC. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Other means of producing specific hybridization probes for fsec include the cloning of nucleic acid sequences encoding FSEC and FSEC derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding FSEC and FSEC derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the fsec sequence or any portion thereof.

The nucleotide sequence can be used to construct an assay to detect inflammation or disease associated with abnormal levels of expression of FSEC. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation and/or disease.

The nucleotide sequence for fsec can be used to construct hybridization probes for mapping that gene. The nucleotide sequence provided herein may be mapped to a chromosome and specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, NYC.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of fsec on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

Nucleotide sequences encoding FSEC may be used to produce purified FSEC using well known methods of recombinant DNA technology. Among the many publications that teach methods for the expression of genes after they have been isolated is Goeddel (1990) Gene Expression Technology, Methods and Enzymology, Vol 1 85, Academic Press, San Diego. FSEC may be expressed in a variety of host cells, either prokaryotic or eukaryotic. Host cells may be from the same species in which fsec nucleotide sequences are endogenous or from a different species. Advantages of producing FSEC by recombinant DNA technology include obtaining adequate amounts of the protein for purification and the availability of simplified purification procedures.

Cells transformed with DNA encoding FSEC may be cultured under conditions suitable for the expression of the FSEC and the recovery of the protein from the cell culture. FSEC produced by a recombinant cell may be secreted or may be contained intracellularly, depending on the particular genetic construction used. In general, it is more convenient to prepare recombinant proteins in secreted form. Purification steps vary with the production process and the particular protein produced.

In addition to recombinant production, FSEC fragments may be produced by direct peptide synthesis using solid-phase techniques (cf Stewart et al (1969) Solid-Phase Peptide Synthesis, WH Freeman Co, San Francisco; Merrifield J (1963) J Am Chem Soc 85:2149–2154. In vitro protein synthesis may be performed using manual techniques or by automation. Automated synthesis may be achieved, for example, using Applied Biosystems 431A Peptide Synthesizer (Foster City, Calif.) in accordance with the instructions provided by the manufacturer. Various fragments of FSEC may be chemically synthesized separately and combined using chemical methods to produce the full length molecule.

FSEC for antibody induction does not require biological activity; however, it must be immunogenic. Peptides used to induce specific antibodies may have an aa sequence consisting of at least five aa, preferably at least 10 aa. They should mimic a portion of the aa sequence of the protein and may contain the entire aa sequence of a small naturally occurring molecule like FSEC. Short stretches of FSEC aa may be fused with those of another protein such as keyhole limpet hemocyanin and the chimeric molecule used for antibody production.

Antibodies specific for FSEC may be produced by inoculation of an appropriate animal with the polypeptide or an antigenic fragment. An antibody is specific for FSEC if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse W D et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding FSEC.

An additional embodiment of the subject invention is the use of FSEC-specific antibodies, inhibitors, receptors or their analogs as bioactive agents to treat inflammation or disease of the fetal spleen including, but not limited to viral or bacterial infections, including mononucleosis, malaria or AIDS; mechanical injury associated with trauma; diseases affecting immunoregulation such as rheumatoid arthritis or systemic lupus erythematosus; diseases of erythrocytes or blood flow including sickle cell anemia and β thalassemia; infiltrative diseases such as leukemias and lymphomas; or other physiologic and pathologic problems which affect the function of the organ.

Bioactive compositions comprising agonists, antagonists, receptors or inhibitors of FSEC may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems of the spleen.

The examples below are provided to illustrate the subject invention. These examples are provided by way of illustration and are not included for the purpose of limiting the invention.

Examples

I Isolation of mRNA and Construction of cDNA Libraries

The fsec cDNA sequence was identified among the sequences comprising the human fetal spleen library. This library was constructed from pooled human fetal spleen tissues by Stratagene Inc. (Cat. #937205; 11011 N Torrey Pines Rd, La Jolla, Calif. 92037). cDNA synthesis was primed using oligo dT hexamers, and synthetic adapter oligonucleotides were ligated onto cDNA ends enabling its insertion into the UNI-ZAP™ vector system (Stratagene Inc). This vector allows high efficiency unidirectional (sense orientation) lambda library construction and the convenience of a plasmid system with blue/white color selection to detect clones with cDNA insertions.

The quality of the each cDNA library was screened using either DNA probes or antibody probes, and then the pBluescript® phagemid (Stratagene Inc) was rapidly excised in living cells. The phagemid allows the use of a plasmid system for easy insert characterization, sequencing, site-directed mutagenesis, the creation of unidirectional deletions and expression of fusion proteins. Phage particles from each library were infected into the E coli host strain XL1-BLUE® (Stratagene Inc.). The high transformation efficiency of XL1-BLUE increases the probability of obtaining rare, under-represented clones from the cDNA library.

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBluescript plasmid and the cDNA insert. The phagemid DNA was released from the cells and purified, then used to re-infect fresh bacterial host cells (SOLR, Stratagene Inc), where the double-stranded phagemid DNA was produced. Because the phagemid carries the gene for β-lactamase, the newly transformed bacteria were selected on medium containing ampicillin.

Phagemid DNA was purified using the QIAWELL-8 Plasmid Purification System from QIAGEN® DNA Purification System (QIAGEN Inc, 9259 Eton Ave, Chatsworth, Calif. 91311). This technique provides a rapid and reliable high-throughput method for lysing the bacterial cells and isolating highly purified phagemid DNA. The DNA eluted from the purification resin was suitable for DNA sequencing and other analytical manipulations.

III Sequencing of cDNA Clones

The cDNA inserts from random isolates of the human fetal spleen library were sequenced in part. Methods for DNA sequencing are well known in the art. Conventional enzymatic methods employed DNA polymerase Klenow fragment, SEQUENASE® (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 and the Applied Biosystems 373 DNA sequencer).

IV Homology Searching of cDNA Clones and Deduced Protein

Each sequence so obtained was compared to sequences in GenBank using a search algorithm developed by Applied Biosystems Inc. and incorporated into the INHERIT™ 670 Sequence Analysis System. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

The nucleotide and amino acid sequences for the fetal spleen expressed chemokine, FSEC, are shown in FIG. 1. Inherit analysis revealed that Incyte clone 29592.db (see FIG. 2), contained a significant portion of the chemokine claimed in this invention. The missing 5' sequence was obtained using PCR technology well known in the art. In the first round of amplification, one oligomer (specific to a portion of the chemokine 29592.db), TCC TTC CTT CTG GTC CTC GGT TCC, and the other (specific to the vector containing the fetal spleen cDNA inserts), GGA MC AGC TAT GAC CAT G, were used to amplify the missing sequence. In the second round of amplification, a set of nested oligomers (ie., one internal to the previous 5' oligomer) consisting of the nucleotides, CTT GGA ATT CAC TCC GGG CTC CCT CTG CAC G, and the vector sequence (already shown above) were used to further amplify the cDNA. The missing 5' sequence was isolated using ECO RI (which digests the DNA within the underlined restriction site in the third oligomer above) and electrophoresis and spliced to the 3' portion of the chemokine sequence from 29592.db. The full length molecule designated 29592 was resequenced as described below.

V Identification and Full Length Sequencing of the Gene

Figure 4:
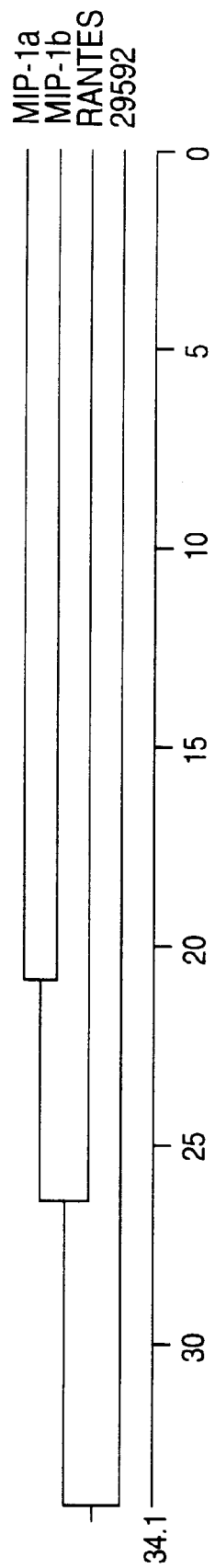
FIG. 4 shows a relatedness tree of human C-C chemokines. The phylogenetic tree was generated by phylogenetic tree program of DNASTAR software (DNASTAR Inc, Madison Wis.) using the Clustal method with the PAM250 residue weight table.

From all of the randomly picked and sequenced clones of the human fetal spleen library, the fsec sequence were homologous to but clearly different from any known C-C chemokine molecule. The complete nucleotide sequence for fsec is shown as Incyte clone 29592. When all three possible predicted translations of the sequence were searched against protein databases such as SwissProt and PIR, no exact matches were found to the possible translations of fsec. FIG. 2 shows the comparison of FSEC with other β chemokine molecules. The substantial regions of homology among these molecules which includes the definitive C-C motif are shaded. The phylogenetic analysis (FIG. 4) shows how closely fsec is related to other well characterized human C-C chemokines. The most related of these molecules cluster together at the right hand side of the figure.

VI Antisense Analysis

Knowledge of the correct, complete cDNA sequences of novel expressed chemokine genes will enable their use in antisense technology in the investigation of gene function. Either oligonucleotides, genomic or cDNA fragments comprising the antisense strand of fsec can be used either in vitro or in vivo to inhibit expression of the specific protein. Such technology is now well known in the art, and probes can be designed at various locations along the nucleotide sequence. By treatment of cells or whole test animals with such antisense sequences, the gene of interest can be effectively turned off. Frequently, the function of the gene can be ascertained by observing behavior at the cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of FSEC

Expression of fsec may be accomplished by subcloning the cDNA into an appropriate expression vector and transfecting this vector into an appropriate expression host. In this particular case, the cloning vector previously used for the generation of the tissue library also provides for direct expression of the included sequence in *E coli*. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

Fsec cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae,* and bacteria such as *E coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced FSEC can be recovered from the conditioned medium and analyzed using chromatographic methods known in the art.

VIII Isolation of Recombinant FSEC

FSEC may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen, San Diego Calif.) between the purification domain and the fsec sequence may be useful to facilitate expression of FSEC.

IX Production of FSEC-Specific Antibodies

Two approaches are utilized to raise antibodies to FSEC, and each approach is useful for generating either polyclonal or monoclonal antibodies. In one approach, denatured FSEC from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

Figure 3:
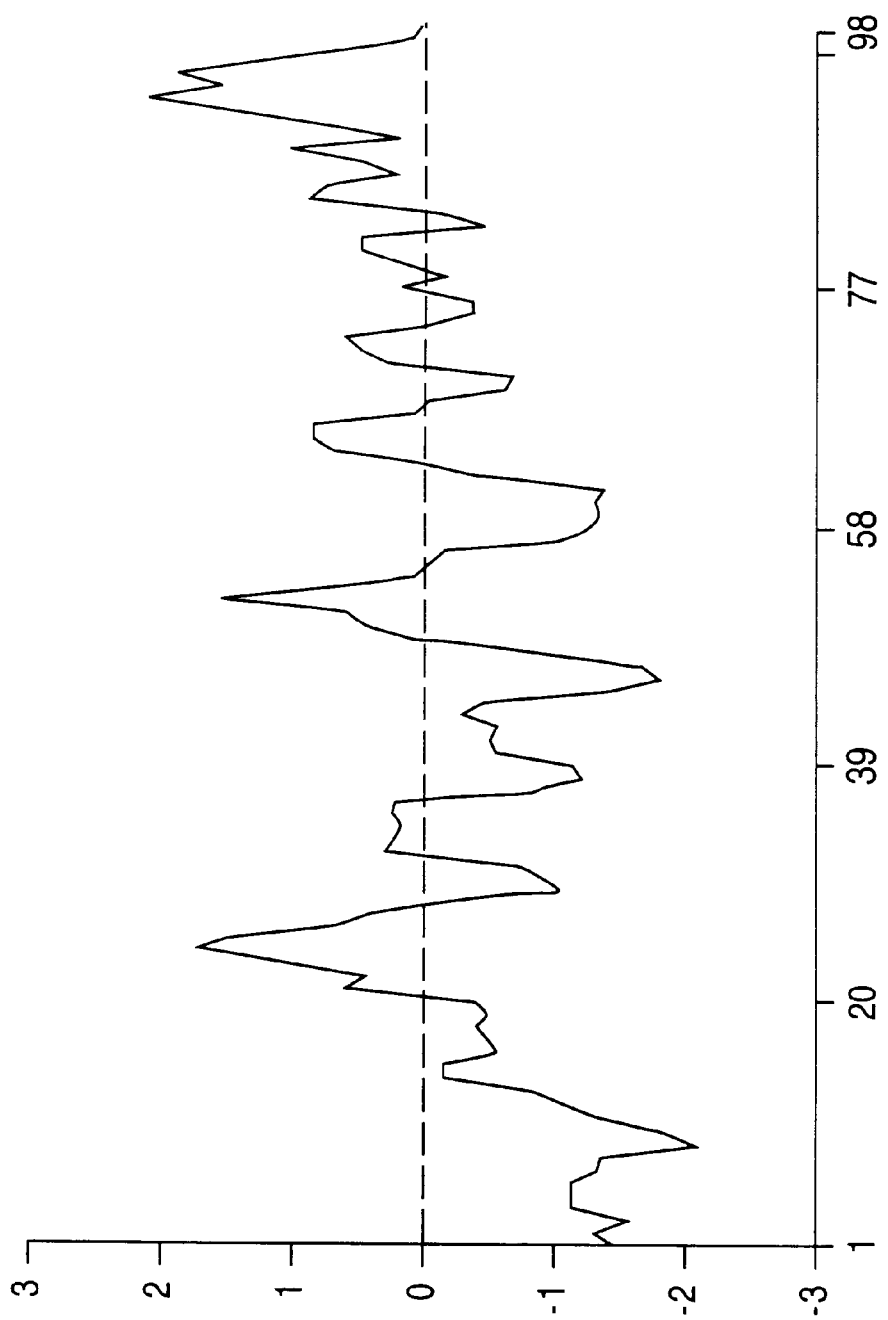
FIG. 3 displays an analysis of FSEC hydrophobicity based on the predicted aa sequence and composition.

In the second approach, the amino acid sequence of FSEC, as deduced from translation of the cDNA, is analyzed to determine regions of high immunogenicity. Oligopeptides comprising hydrophilic regions, as shown in FIG. 3, are synthesized and used in suitable immunization protocols to raise antibodies. Analysis to select appropriate epitopes is described by Ausubel FM et al (1989, Current Protocols in Molecular Biology, John Wiley & Sons, NYC). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques.

Hybridomas of interest are detected by screening with labeled FSEC to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled FSEC, 1 mg/ml. Clones producing antibodies will bind a quantity of labeled FSEC which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least 10 e8 Me-1, preferably 10e9 to 10e10 or stronger, will typically be made by standard procedures as described in Harlow and Lane (1988) Antibodies: A Laboratory Manual. Cold Spring Harbor Laboratory NY; and in Goding (1986) Monoclonal Antibodies: Principles and Practice, Academic Press, NYC, both incorporated herein by reference.

X Diagnostic Test Using FSEC-Specific Antibodies

Particular FSEC antibodies are useful for the diagnosis of prepathologic conditions, and chronic or acute diseases which are characterized by differences in the amount or distribution of FSEC. To date, FSEC has only been found in the human fetal spleen library and is thus specific for abnormalities or pathologies which affect the spleen.

Diagnostic tests for FSEC include methods utilizing the antibody and a label to detect FSEC in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241.

Also, recombinant immunoglobulins may be produced as shown in U.S. Pat. No. 4,816,567, incorporated herein by reference.

A variety of protocols for measuring soluble or membrane-bound FSEC, using either polyclonal or monoclonal antibodies specific for that FSEC are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on FSEC is preferred, but a competitive binding assay may be employed. These assays are described, among other places, in Maddox, D E et al (1983, J Exp Med 158:1211).

XI Purification of Native FSEC Using Specific Antibodies

Native or recombinant FSEC was purified by immunoaffinity chromatography using antibodies specific for FSEC. In general, an immunoaffinity column is constructed by covalently coupling the anti-FSEC antibody to an activated chromatographic resin.

Polyclonal immunoglobulins are prepared from immune sera either by precipitation with ammonium sulfate or by purification on immobilized Protein A (Pharmacia LKB Biotechnology, Piscataway, NJ). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such an immunoaffinity column was utilized in the purification of FSEC by preparing a fraction from cells containing FSEC in a soluble form. This preparation was derived by solubilization of the whole cell or of a subcellular fraction obtained via differential centrifugation by the addition of detergent or by other methods well known in the art. Alternatively, soluble FSEC containing a signal sequence may be secreted in useful quantity into the medium in which the cells are grown.

A soluble FSEC-containing preparation was passed over the immunoaffinity column, and the column was washed under conditions that allow the preferential absorbance of FSEC (eg, high ionic strength buffers in the presence of detergent). Then, the column was eluted under conditions that disrupt antibody/FSEC binding (e.g., a buffer of pH 2–3 or a high concentration of a chaotrope such as urea or thiocyanate ion), and FSEC was collected.

XII Determination of FSEC-Induced Chemotaxis or Cell Activation

The chemotactic activity of FSEC is measured in a 48-well microchemotaxis chamber (Falk W R et al (1980) J Immunol Methods 33:239). In each well, two compartments are separated by a filter that allows the passage of cells in response to a chemical gradient. Cell culture medium such as RPMI 1640 (Sigma, St. Louis Mo.) containing FSEC is placed on one side of a filter, usually polycarbonate, and cells suspended in the same media are placed on the opposite side of the filter. Sufficient incubation time is allowed for the cells to traverse the filter in response to the concentration gradient across the filter. Filters are recovered from each well, and cells adhering to the side of the filter facing FSEC are typed and quantified.

The specificity of the chemoattraction is determined by performing the chemotaxis assay on specific populations of cells. First, blood cells obtained from venipuncture are fractionated by density gradient centrifugation and the chemotactic activity of FSEC is tested on enriched populations of neutrophils, peripheral blood mononuclear cells, monocytes and lymphocytes. Optionally, such enriched cell populations are further fractionated using CD8+ and CD4+ specific antibodies for negative selection of CD4+ and CD8+ enriched T-cell populations, respectively.

Another assay elucidates the chemotactic effect of FSEC on activated T-cells. There, unfractionated T-cells or fractionated T-cell subsets are cultured for 6 to 8 hours in tissue culture vessels coated with CD-3 antibody. After this CD-3 activation, the chemotactic activity of FSEC is tested as described above. Many other methods for obtaining enriched cell populations are known in the art.

Some chemokines also produce a non-chemotactic cell activation of neutrophils and monocytes. This is tested via standard measures of neutrophil activation such as actin polymerization, increase in respiratory burst activity, degranulation of the azurophilic granule and mobilization of $Ca^{++}$ as part of the signal transduction pathway. The assay for mobilization of $Ca^{++}$ involves preloading neutrophils with a fluorescent probe whose emission characteristics have been altered by $Ca^{++}$ binding. When the cells are exposed to an activating stimulus, $Ca^{++}$ flux is determined by observation of the cells in a fluorometer. The measurement of $Ca^{++}$ mobilization has been described in Grynkievicz G et al. (1985) J Biol Chem 260:3440, and McColl S et al. (1993) J Immunol 150:4550–4555, incorporated herein by reference.

Degranulation and respiratory burst responses are also measured in monocytes (Zachariae COC et al. (1990) J Exp Med 171:2177–82). Further measures of monocyte activation are regulation of adhesion molecule expression and cytokine production (Jiang Y et al. (1992) J Immunol 148:2423–8). Expression of adhesion molecules also varies with lymphocyte activation (Taub D et al. (1993) Science 260:355–358).

XIII Drug Screening

This invention is particularly useful for screening compounds by using FSEC polypeptide or binding fragment thereof in any of a variety of drug screening techniques. The FSEC polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between FSEC or a fragment and the agent being tested. Alternatively, one can examine the diminution in complex formation between FSEC and its target cell, monocyte, etc. caused by the agent being tested.

Thus, the present invention provides methods of screening for drugs or any other agents which can affect inflammation and disease. These methods comprise contacting such an agent with an FSEC polypeptide or fragment thereof and assaying (i) for the presence of a complex between the agent and the FSEC polypeptide or fragment, or (ii) for the presence of a complex between the FSEC polypeptide or fragment and the cell, by methods well known in the art. In such competitive binding assays, the FSEC polypeptide or fragment is typically labeled. After suitable incubation, free FSEC polypeptide or fragment is separated from that present in bound form, and the amount of free or uncomplexed label is a measure of the ability of the particular agent to bind to FSEC or to interfere with the FSEC/cell complex.

Another technique for drug screening provides high throughput screening for compounds having suitable binding affinity to the FSEC polypeptides and is described in detail in EPA 84/03564, published on Sept. 13, 1984, incorporated herein by reference. Briefly stated, large numbers of different small peptide test compounds are synthesized on a solid substrate, such as plastic pins or some other surface. The peptide test compounds are reacted with FSEC polypeptide and washed. Bound FSEC polypeptide is then detected by methods well known in the art. Purified FSEC can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding FSEC specifically compete with a test compound for binding to FSEC polypeptide or fragments thereof. In this manner, the antibodies can be used to detect the presence of any peptide which shares one or more antigenic determinants with FSEC.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous chemokine-like molecules or to identify efficient inhibitors. Useful examples of rational drug design may include molecules which have improved activity or stability as shown by Braxton S and Wells J A (1992 Biochemistry 31:7796–7801) or which act as inhibitors, agonists, or antagonists of native peptides as shown by Athauda S B et al (1993 J Biochem 11 3:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the FSEC amino acid sequence provided herein will provide guidance to those employing computer modeling techniques in place of or in addition to x-ray crystallography.

XV Identification of FSEC Receptors

Purified FSEC is useful for characterization and purification of specific cell surface receptors and other binding molecules. Cells which respond to FSEC by chemotaxis or other specific responses are likely to express a receptor for FSEC. Radioactive labels may be incorporated into FSEC by various methods known in the art. A preferred embodiment is the labeling of primary amino groups in FSEC with 1251 Bolton-Hunter reagent (Bolton, A E and Hunter, W M (1973) Biochem J 133:529), which has been used to label other chemokines without concomitant loss of biological activity (Hebert C A et al (1991) J Biol Chem 266:18989; McColl S et al (1993) J Immunol 150:4550–4555). Receptor-bearing cells are incubated with labeled FSEC. The cells are then washed to removed unbound FSEC, and receptor-bound FSEC is quantified. The data obtained using different concentrations of FSEC are used to calculate values for the number and affinity of receptors.

Labeled FSEC is useful as a reagent for purification of its specific receptor. In one embodiment of affinity purification, FSEC is covalently coupled to a chromatography column. Receptor-bearing cells are extracted, and the extract is passed over the column. The receptor binds to the column by virtue of its biological affinity for FSEC. The receptor is recovered from the column and subjected to N-terminal protein sequencing. This amino acid sequence is then used to design degenerate oligonucleotide probes for cloning the receptor gene.

In an alternate method, mRNA is obtained from receptor-bearing cells and made into a cDNA library. The library is transfected into a population of cells, and those cells expressing the receptor are selected using fluorescently labeled FSEC. The receptor is identified by recovering and sequencing recombinant DNA from highly labeled cells.

In another alternate method, antibodies are raised against the surface of receptor-bearing cells, specifically monoclonal antibodies. The monoclonal antibodies are screened to identify those which inhibit the binding of labeled FSEC. These monoclonal antibodies are then used in affinity purification or expression cloning of the receptor.

Soluble receptors or other soluble binding molecules are identified in a similar manner. Labeled FSEC is incubated with extracts or other appropriate materials derived from the spleen. After incubation, FSEC complexes larger than the size of purified FSEC are identified by a sizing technique such as size exclusion chromatography or density gradient centrifugation and are purified by methods known in the art. The soluble receptors or binding protein(s) are subjected to N-terminal sequencing to obtain information sufficient for database identification, if the soluble protein is known, or for cloning, if the soluble protein is unknown.

XVI Use and Administration of FSEC

Antibodies, inhibitors, receptors or antagonists of FSEC (or other treatments for excessive FSEC production, hereinafter abbreviated TEC), can provide different effects when administered therapeutically. TECs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, receptor or antagonist being formulated and the condition to be treated. Characteristics of TEC include solubility of the molecule, half-life and antigenicity/immunogenicity; these and other characteristics may aid in defining an effective carrier. Native human proteins are preferred as TECs, but organic or synthetic molecules resulting from drug screens may be equally effective in particular situations.

TECs may be delivered by known routes of administration including but not limited to topical creams and gels; transmucosal spray and aerosol, transdermal patch and bandage; injectable, intravenous and lavage formulations; and orally administered liquids and pills, particularly formulated to resist stomach acid and enzymes. The particular formulation, exact dosage, and route of administration will be determined by the attending physician and will vary according to each specific situation.

Such determinations are made by considering multiple variables such as the condition to be treated, the TEC to be administered, and the pharmacokinetic profile of the particular TEC. Additional factors which may be taken into account include disease state (e.g. severity) of the patient, age, weight, gender, diet, time of administration, drug combination, reaction sensitivities, and tolerance/response to therapy. Long acting TEC formulations might be administered every 3 to 4 days, every week, or once every two weeks depending on half-life and clearance rate of the particular TEC.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different TECs and that administration targeting the spleen may necessitate delivery in a manner different from that to another organ or tissue.

It is contemplated that conditions or diseases of the spleen which activate monocytes, macrophages, basophils, eosinophils or other leukocytes may precipitate damage that is treatable with TECs. These conditions or diseases may be specifically diagnosed by the tests discussed above, and such testing should be performed in suspected cases of viral or bacterial infections including mononucleosis, malaria or AIDS; mechanical injury associated with trauma; diseases affecting immunoregulation such as rheumatoid arthritis or systemic lupus erythematosis; diseases of erythrocytes or blood flow including sickle cell anemia and $\beta$ thalassemia; infiltrative diseases such as leukemias and lymphomas; or other physiologic and pathologic problems which affect the function of the organ.

All publications and patents mentioned in the above specification are herein incorporated by reference. The foregoing written specification is considered to be sufficient to enable one skilled in the art to practice the invention. Indeed, various modifications of the above described modes for carrying out the invention which are obvious to those skilled in the field of molecular biology or related fields are intended to be within the scope of the following claims.

We claim:

1. A purified fetal spleen expressed chemokine (FSEC) polypeptide as in SEQ ID NO. 2.

2. A fetal spleen expressed chemokine polypeptide, having SEQ ID NO: 2, said polypeptide provided by a method comprising the steps of:

a. culturing a host cell containing a polynucleotide sequence which encodes said polypeptide; and b. recovering the polypeptide from the host cell culture.

* * * * *